United States Patent [19]

Nick et al.

[11] Patent Number: 5,656,475
[45] Date of Patent: Aug. 12, 1997

[54] USE OF LYMPHOCYTES TRANSFORMED WITH HERPESVIRUS SAIMIRI IN A PROCESS FOR REPLICATING VIRUSES OF THE HIV TYPE WHICH CAUSE IMMUNE DEFICIENCY

[75] Inventors: Sigrid Nick, Forchheim; Helmut Fickenscher, Fürth-Mannhof; Brigitte Biesinger-Zwosta, Uttenreuth; Gerhard Jahn, Tübingen; Bernhard Fleckenstein, Wiesenthau, all of Germany

[73] Assignee: Behringwerke Aktiengesellschaft, Marburg, Germany

[21] Appl. No.: 208,299

[22] Filed: Mar. 10, 1994

[30] Foreign Application Priority Data

Mar. 12, 1993 [DE] Germany .................... 43 07 970.9

[51] Int. Cl.$^6$ .................................... C12Q 1/70
[52] U.S. Cl. .............. 435/235.1; 435/693; 435/70.1; 435/70.3; 435/91.1; 435/91.33; 435/239; 435/373; 424/93.21; 424/188.1; 424/208.1
[58] Field of Search ................... 435/5, 235.1, 239, 435/240.1, 252.3, 974, 69.3, 70.1, 70.3, 91.1, 91.33, 240.2, 240.27; 424/93.21, 188.1, 208.1, 229.1

[56] References Cited

FOREIGN PATENT DOCUMENTS

WO 90/04020  4/1990  WIPO.

OTHER PUBLICATIONS

Nick et al, Virology, 194, "Herpesvirus Saimiri Transformed Human T Cell Lines: A Permissive System for Human Immunodeficiency Viruses", 875–877 (1993).
Nabel et al, Science, vol. 239, "Alternative Mechanisms for Activation of Human Immunodeficiency Virus Enhancer in T Cells", 1299–1302, Mar. 1988.
Ensoli et al., The EMBO Journal, vol. 8, No. 10, "Human Herpes Virus–6 Increases HIV–1 Expression in Co–Infected T Cells via Nuclear Factors Binding to the HIV–1 Enhancer", pp. 3019–3027, 1989.
Horvat et al., Journal of Virology, vol. 65, No. 6, pp. 2895–2902, Jun. 1991.
Biesinger et al., Virology (176) 505–514, 1990, "The Divergence between Two Oncogenic Herpesvirus saimiri Strains in a Genomic Region related to the Transforming Phenotype".
Grassmann et al., Proc. Natl. Acad. Sci. USA, vol. 86, pp. 3351–3355, May 1989, "Transformation to continuous growth of primary hu man T lymphocytes by human T–cell leukemia virus type I X–region genes transduced by a Herpesvirus saimiri vector".
Biesinger et al., Proc. Natl. Acad. Sci. USA, vol. 89, pp. 3116–3119, Apr. 1992, "Stable growth transformation of human T lymphocytes by Herpesvirus saimiri".

Grassmann et al., Journal of Virology, pp. 1818–1821, Apr. 1989, "Selectable Recombinat Herpesvirus Saimiri Is Capable of Human T–Cell Line".
Mittrücker et al., CD2–Mediated Autocrine Growth of Herpes Virus Saimiri–Transformed Human T Lymphocytes, The Journal of Experimental Medicine, vol. 176, No. 3, pp. 909–913, Sep. 1, 1992.
Fickenscher et al., Viral Genes Involved in Stable Growth Transformation of Human T–Lymphocytes, Chemical Abstracts, vol. 122, No. 17, Apr. 24, 1995, p. 728.
Bröker et al., Immortalization of Human T Cell Clones by Herpevirus Saimiri, The Journal of Immunology, vol. 151, No. 3, pp. 1184–1192, Aug. 1, 1993.
Fickenscher et al., Viral Expression During Growth Transformation of Human T–Lymphocytes by Herpesvirus Saimiri, 24th Meeting of the Society for Immunology, Immunobiol, vol. 189, No. 1–2, Sep. 1993.
Eberlein et al., "Expression Of Human Immunodeficiency Virus (HIV) In Naturally Infected Peripheral Blood Mononuclear Cells: Comparison Of A Standard Co–culture Technique With A Newly Developed Microculture Method", Virus Res., 19:153–162 (1991).
Clavel et al., "Molecular Cloning And Polymorphism Of The Human Immune Deficiency Virus Type 2", Nature, 324:691–695 (1986).
Bohm et al., "Detection of Viral Surface Antigens On HIV–2ben Infected Human Tumor Cell Lines By Flow Cytometry", Cytometry, 13:259–266 (1992).
Popovic et al., "Detection, Isolation, and Continuous Production of Cytopathic Retroviruses (HTLV–III) From Patients with AIDS and Pre–Aids," Science, 224:497–500 (1984).
Biesinger et al., "Stable Growth Transformation Of Human T Lymphocytes By Herpesvirus Saimiri", Proc. Natl. Acad. Sci., 89:3116–3119 (1992).
Nick et al., "Detection of HIV–2 Infection In a Nepalese Individual", AIFO, 6:307–309 (1993).
Bruckner et al., "The Sequences of the Membrane–Modifying Peptide Antibotic Trichotoxin A–40," Angew. Chem. Int. Ed. Engl. 18(6):476–477 (1979).
Przybylski et al., "Elucidation of Structure and Microheterogeneity of the Polypeptide Antibiotics Paracelsin and trichotoxin A–50 by Fast Atom Bombardment Mass Spectrometry in Combination with Selective in situ Hydrolysis," Biomedical Mass Spectrometry, 11(11):569–582 (1984).

*Primary Examiner*—Christine M. Nucker
*Assistant Examiner*—Laurie Scheiner
*Attorney, Agent, or Firm*—Finnegan, Henderson, Farabow, Garrett & Dunner, L.L.P.

[57] ABSTRACT

A process is disclosed for replicating viruses of the HIV type which cause immune deficiency, in which process lymphocytes are employed which have been transformed with herpesvirus saimiri.

7 Claims, 3 Drawing Sheets

USE OF LYMPHOCYTES TRANSFORMED WITH HERPESVIRUS SAIMIRI IN A PROCESS FOR REPLICATING VIRUSES OF THE HIV TYPE WHICH CAUSE IMMUNE DEFICIENCY

It has become clear in recent years that infection with viruses of the HIV type which cause immune deficiency represents a serious problem the solution to which is the subject of intensive research.

It has emerged from world-wide research efforts that the immune deficiency disease which is given the designation AIDS is not caused simply by one single virus type belonging to the RNA viruses, but rather that the disease is caused by at least two relatively large groups of HIV viruses. The individual causative agents exhibit a high degree of genetic variability and can for the most part be assigned to one of the groups of HIV viruses which are already known.

Since the HIV viruses do not have at their disposal a metabolism of their own, they are replicated in the laboratory, for the purposes of research or diagnosis, using cell lines.

Various cell lines are known which can be used for replicating viruses of the HIV type which cause immune deficiency. However, it has emerged that various virus strains and virus isolates, in particular those which originate from asymptomatic, seropositive patients, cannot be replicated, or can only be replicated very poorly, in the known cell lines. Viruses of this type are therefore frequently grown on primary lymphocyte cultures which must be freshly prepared on each occasion. The virus yield which is obtained under these circumstances is low and the primary cells vary in their replication properties.

The object of the present invention is therefore, to make available a process for replicating viruses of the HIV type which cause immune deficiency, which process can be used to replicate, in particular, only weakly replicating HIV strains or primary clinical isolates.

The process according to the invention is one in which the viruses are replicated with the aid of lymphocytes which have been transformed with herpesvirus saimiri.

Herpesvirus saimiri induces T cell lymphomas in various types of New World monkeys and in rabbits. Herpesvirus saimiri may frequently be found in South American squirrel monkeys (*Saimiri ciureus*), but is not pathogenic in this species. Strains of herpesvirus saimiri, subgroup C, effectively transform human lymphocytes from the thymus or the peripheral blood of human donors into continuously replicating T cell lines (Proc. Natl. Acad. Sci. USA, Vol. 89, pp. 3116–3119, April 1992).

The lymphocytes which are usable within the scope of the process according to the invention are preferably lymphocytes which originate from the human thymus, human peripheral blood or human umbilical cord blood.

It is possible to prepare suitable lymphocytes by, for example, isolating the cells by means of centrifugation through Histopaque density gradients (1.1 g/ml; Pharmacia) in order to obtain mononuclear cells which are subsequently stimulated with phytohemagglutinin P. In the case of isolation from the blood, on the other hand, the erythrocytes can be separated off by dextran sedimentation and the leucocytes then sedimented from the supernatant. Thymocytes are isolated from minced thymus tissue which is customarily obtained from children who have undergone a heart surgery.

Stimulated and unstimulated cells were grown in suitable culture vessels at a density of $1 \times 10^6$ cells per ml and inoculated with $10^4$ to $10^6$ infectious doses of herpesvirus saimiri. The phytohemagglutinin-stimulated cells were additionally supplemented with recombinant interleukin 2 (50 U/ml). The formation of infectious virus was tested for by co-cultivating the lymphocytes with monkey kidney cells.

Cells possess structures on their surfaces which have particular functions, such as, for example, various receptors. These surface structures are used for identifying the cells.

It has now emerged that those cell lines are particularly suitable for replicating viruses of the HIV type which possess the so-called $CD4^+$ molecule on their surface.

Within the scope of the process according to the invention, cells transformed with herpesvirus saimiri are preferably employed which are selected from the group comprising the following cell lines: PB-W, CB-15 and Lucas (PNAS, 89, pp. 3116–3119, April 1992) or PB-M, CB-23 and Kesting (Simmer, B. Berthold, S., Biesinger, B., Müller-Fleckenstein, I., Kalden, J., Platzer, E., Fleckenstein, B., manuscript in preparation).

The process according to the invention can particularly advantageously be used for replicating those viruses of the HIV type which otherwise can only be replicated with great difficulty. Many strains can only be grown in the laboratory with considerable difficulty. This applies, in particular, to those strains which originate from patients who are seropositive while being clinically free of symptoms.

The present process represents a very advantageous system for cultivating viruses which cause immune deficiency. Human lymphoid cells which are transformed with herpesvirus saimiri and which are CD4-positive are highly sensitive to infection with the prototype HIV strains HIV-$1_{IIIB}$ and HIV-$2_{ROD}$ and then produce large quantities of virus. These cell lines are very particularly suitable for replicating HIV-2 isolates which have a limited cell spectrum and which originate from asymptomatic patients.

In addition to this, the cells transformed with herpesvirus saimiri offer advantages when co-cultivated with donor lymphocyte cells from peripheral blood. In the co-cultivation, lymphocytes which are isolated from a donor, who is preferably HIV-positive, are grown together with other cells or cell lines. The cells transformed with herpesvirus saimiri exhibit improved replication when they are brought into contact with allogenic lymphocytes from peripheral blood. It is possible for this mechanism to be controlled by way of interactions of the CD2 and CD58 molecules, thereby giving rise to increased HIV production. It was possible to maintains the cell lines transformed with herpesvirus saimiri stably in culture for at least one year and it was not possible to detect any secretion of infectious herpesvirus saimiri. It is assumed, therefore, that the HIV virus does not induce production of herpesvirus saimiri. The process according to the invention is particularly useful for replicating HIV viruses in large amounts, in particular HIV-2 isolates from asymptomatic patients.

EXAMPLE 1

Various cell lines which express the CD4 molecule were examined. The control which was used was the cell line P1084 which, while expressing the surface marker molecule CD8 does not express the CD4 molecule. Each culture of $4 \times 10^6$ cells was infected with 1 ml of cell-free virus suspension of HIV-$1_{IIIB}$ (Popovic et al., Science, 224 pp. 497–500, 1984), HIV-$2_{ROD}$ (Clavel et al., Nature, 324, pp. 691–695, 1986) or HIV-$2_{NEP}$ (Nick, S., Häfner, Y., Diniz, C. A., Jahn, G., Detection of HIV-2 infection in a Nepalese individual, AIFO in press, 1993), as described in more detail in Böhm et al., Cytometry, 13, pp. 259–266, 1992, and then sown in cell culture plates.

The activities of reverse transcriptase (RT) in the suspensions which were used for the infection amounted to 20,000 cpm/ml for HIV-$1_{IIIB}$, 410,000 cpm/ml for HIV-$2_{ROD}$ and 824,000 cpm/ml for HIV-$2_{NEP}$ respectively. In order to determine the HIV replication in these cultures, the reverse transcriptase activity was measured in the culture supernatants (Böhm et al., Cytometry, 13, pp. 259–266, 1992).

The virus strain HIV-$2_{NEP}$ was recently isolated from an asymptomatic Nepalese patient. This isolate only replicates in MOLT-4 clone 8 cells and in umbilical cord lymphocytes. Prior to this, all attempts to infect other T cells or other macrophage lines had failed, even when a high infectious dose was used.

In addition to this, an investigation was carried out to determine whether cells transformed with herpesvirus saimiri can replace primary lymphocytes in virus isolation. The patient's lymphocytes were separated off and co-cultivated directly with CB-15 or Kesting cells. As an alternative to this, the patient's cells were prestimulated for three days with OKT-3 (Ortho Diagnostic Systems GmbH, Neckargemünd) (Eberlein et al., Virus Res., 19, pp. 153–162, 1991). In parallel to this, HIV-1 was isolated using a standard lymphocyte co-cultivation technique (Eberlein et al., loc. cit.). The production of HIV-1 virus was measured by detecting p24 antigen; this was done in the culture supernatants on days 14, 21 and 28.

The type strains HIV-$1_{IIIB}$ and HIV-$2_{ROD}$ replicated on all cell lines which are transformed with herpesvirus saimiri and which carry the surface marker CD4, and elicited cell death within 16 days. The results of the investigations are depicted in FIGS. 1 and 2. The control cell line P-1084, which does not possess the surface marker CD4, was not susceptible to infection by HIV-1 or HIV-$2_{ROD}$, and survived. The cell lines Kesting and CB-15 produced the highest quantities of HIV-$1_{IIIB}$ and HIV-$2_{ROD}$. Although the cell lines which were transformed with herpesvirus saimiri and infected with HIV-$2_{NEP}$ did not exhibit any cytopathic changes, it was possible to measure high levels of reverse transcriptase activity in the supernatants of all the cell lines which carry the cell marker CD4. These are the cell lines Kesting, Lucas, CB-15, CB-23 and PB-M. The results are depicted in FIG. 3. The reverse transcriptase activity released from CB-23 cells was even higher than that released from the MOLT-4 clone 8 cell line. The results demonstrate that cell lines which are transformed with herpesvirus saimiri and which possess the cell marker CD4$^+$ represent a very productive system for viruses of the HIV-2 type which otherwise only grow weakly.

EXAMPLE 2

In addition, an investigation was carried out to determine whether CB-15 and/or Kesting cell lines can replace lymphocytes isolated from umbilical cord blood for the initial isolation of HIV-1 viruses. Lymphocytes from the peripheral blood of four donors with symptoms of immune deficiency were co-cultivated with lymphocytes from umbilical cord blood, which were stimulated with OKT-3, or with CB-15 or Kesting cell lines. The results are listed in Table I below. In two cases (donor H.F.R. and A.T.), HIV-1 was only successfully isolated in standard lymphocyte co-cultures (L/L). By contrast, in the case of the cultures from patient B.K.H., it was possible to measure high quantities of p24 in CB-15 cultures (L/CB-15) and Kesting cultures (L/Kesting) after two weeks, whereas the standard co-cultivation only yielded HIV-1 after a further two weeks. In addition to this, the quantity of vital antigen produced was ten times greater in the CB-15 and Kesting cell lines.

HIV was isolated twice from patient D.P., with an interval of six weeks. On the first occasion, the donor lymphocytes from peripheral blood were co-cultivated directly with CB-15 and Kesting cells. In the second experiment, the lymphocytes from peripheral blood were prestimulated with OKT-3 nd then co-cultivated (O/L/CB-15; O/L/Kesting). The conventional culture system and the CB-15 cells were successful to a similar degree. Isolation on Kesting cells was only successful when pre-stimulated lymphocytes from peripheral blood were used. In summary, therefore, it can be stated that, although the HIV-1 isolation results were variable, the use of cells transformed with herpesvirus saimiri was superior to the standard procedure in two instances.

TABLE 1

Replication of fresh, clinical HIV-1 isolates using cells transformed with herpesvirus saimiri.

| Patient | Culture | p24 [pg/ml] Day 14 | p24 [pg/ml] Day 21 | p24 [pg/ml] Day 28 |
|---|---|---|---|---|
| H. F. R. | L/L | 63 | 39 | 3644 |
|  | L/CB-15 | 13 | 0 | 0 |
|  | L/Kesting | 0 | 0 | 0 |
| B. H. K. | L/L | 0 | 11 | 5328 |
|  | L/CB-15 | 1487 | 15480 | 14208 |
|  | L/Kesting | 1610 | 14430 | 11544 |
| D. P. | L/L | 336 | 1120 | 1127 |
|  | L/CB-15 | 2498 | 1909 | 1510 |
|  | L/Kesting | 433 | 145 | 17 |
| D. P. | L/L | 1277 | 1421 | 1376 |
|  | O/L/CB-15 | 1199 | 1265 | 1554 |
|  | O/L/Kesting | 155 | 1265 | 1554 |
| A. T. | L/L | 133 | 114 | 97 |
|  | O/L/CB-15 | 12 | 0 | 0 |
|  | O/L/Kesting | 53 | 0 | 0 |

L/L: Standard lymphocyte co-cultivation technique (Eberlein et al., Virus Res. 19, pp. 153–162, 1991)
L/CB-15; L/Kesting: Direct co-cultivation of patient lymphocytes from peripheral blood and CB-15 or Kesting cells
O/L/CB-15; O/L/Kesting: co-cultivation after 3 days of prestimulation with OKT-3

The results obtained in the experiments are depicted in the enclosed figures.

FIG. 1 shows the replication of HIV-$1_{IIIB}$ in T cell lines transformed with herpesvirus saimiri. 4×10$^6$ cells were infected with 1 ml of HIV-$1_{IIIB}$ which consisted of a suspension with a reverse transcriptase activity of 20,000 cpm/ml, as described in Böhm et al., Cytometry, 13, pp. 259–266, 1992. Samples of the culture supernatant were tested for reverse transcriptase activity at the times indicated.

Figure 1:
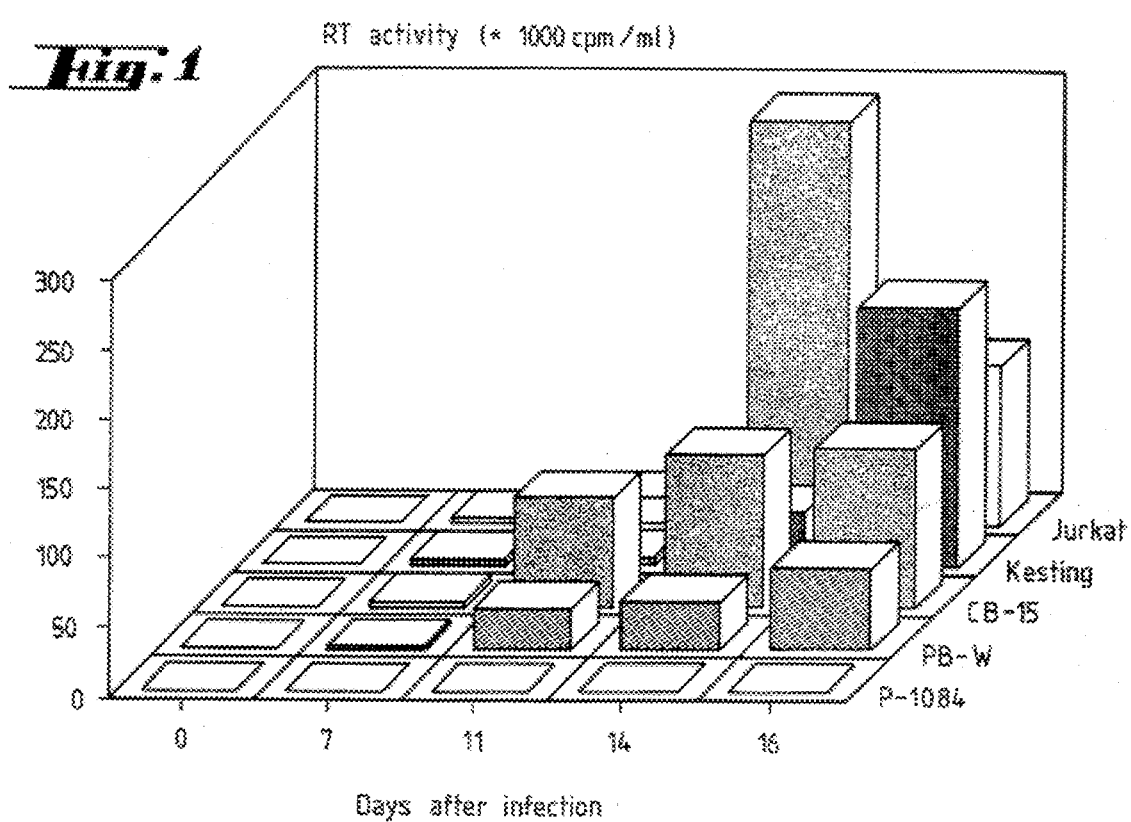
Figure 2:
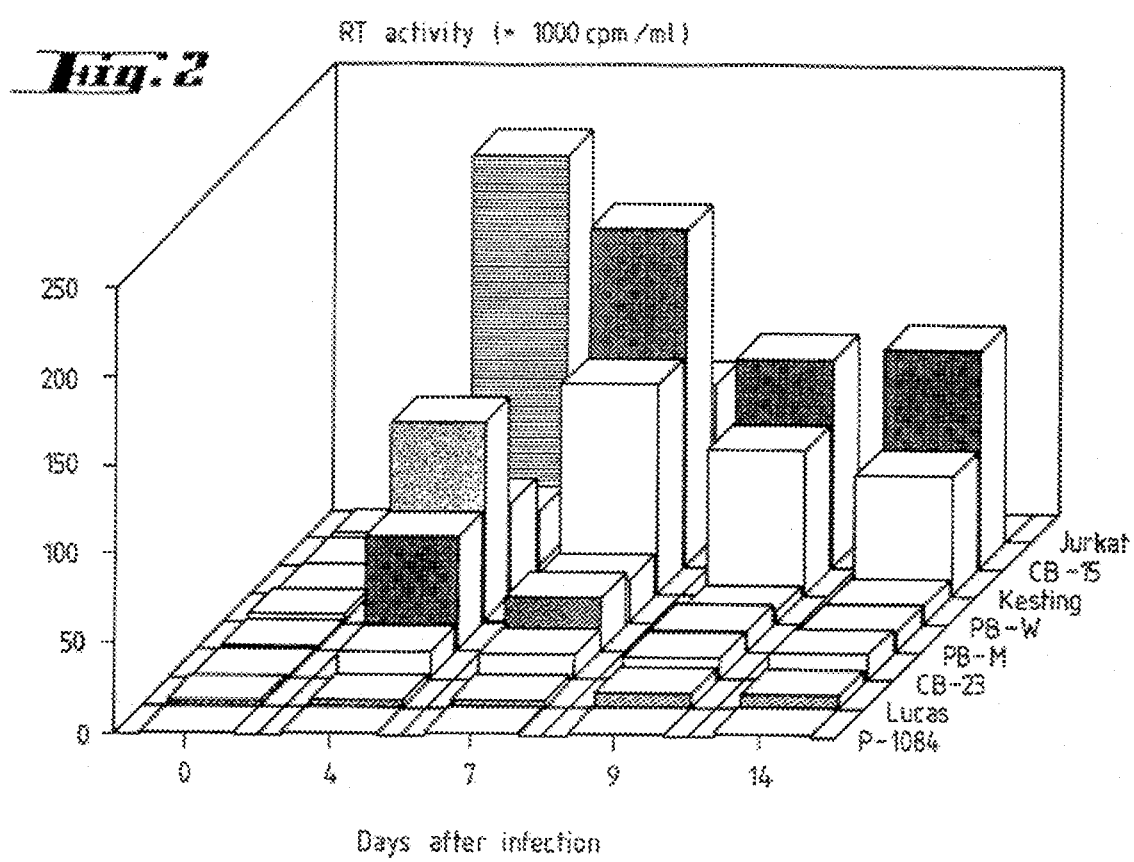
FIG. 2 shows the replication of HIV-$2_{ROD}$ in the T cell lines transformed with herpesvirus saimiri. The reverse transcriptase activity of the HIV-$2_{ROD}$ suspension used for the infection was 410,000 cpm/ml.
Figure 3:
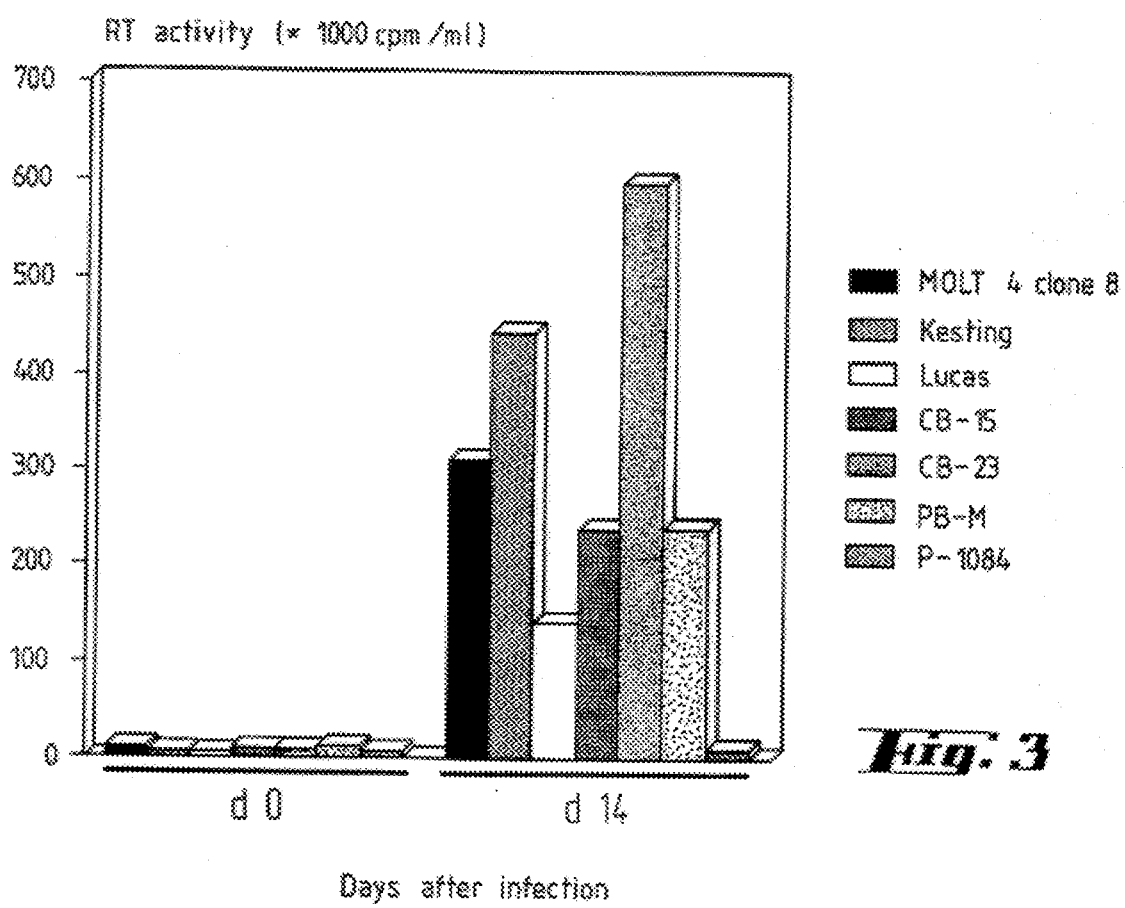
FIG. 3 shows the replication of HIV-$2_{NEP}$ in T cell lines transformed with herpesvirus saimiri. The reverse transcriptase activity of the HIV-$2_{NEP}$ suspension used for the infection was 824,000 cpm/ml.

We claim:

1. A process for replicating viruses of the HIV type which cause immune deficiency, wherein the viruses are replicated with the aid of lymphocytes which have been transformed with herpesvirus saimiri.

2. The process as claimed in claim 1, wherein the human lymphocytes are transformed with herpesvirus saimiri, herpesvirus of group C or of group Non A–Non B.

3. The process as claimed in claim 1, wherein the lymphocytes are CD-4-positive.

4. The process as claimed in claim 1, wherein the human lymphocytes originate from thymus, peripheral blood, umbilical cord blood, lymph nodes, lymphatic vessels, spleen or bone marrow.

5. The process as claimed in claim 4, wherein the lymphocytes transformed with herpesvirus saimiri are selected from the cell lines CB-15, CB-23, PB-W, PB-M, Lucas and Kesting.

6. The process as claimed in claim 1, wherein the viruses of the HIV type which cause immune deficiency are those which originate from asymptomatic, seropositive patients.

7. The process as claimed in claim 1, wherein lymphocytes transformed with herpesvirus saimiri are co-cultivated with other cells.

* * * * *